(12) United States Patent
Ventzki et al.

(10) Patent No.: US 11,662,332 B2
(45) Date of Patent: May 30, 2023

(54) METHOD OF PRODUCING TRANSPARENT BIOLOGICAL PREPARATIONS FOR EXAMINATION BY LIGHT MICROSCOPY

(71) Applicant: Georg-August-Universitaet Goettingen Stiftung Oeffentlichen Rechts, Universitaetsmedizin, Goettingen (DE)

(72) Inventors: Robert Ventzki, Goettingen (DE); Fred S. Wouters-Bunt, Goettingen (DE)

(73) Assignee: GEORG-AUGUST-UNIVERSITAET GOETTINGEN STIFTUNG OEFFENTLICHEN RECHTS, UNIVERSITAETSMEDIZIN, Goettingen (DE)

( * ) Notice: Subject to any disclaimer, the term of this patent is extended or adjusted under 35 U.S.C. 154(b) by 369 days.

(21) Appl. No.: 16/430,997

(22) Filed: Jun. 4, 2019

(65) Prior Publication Data
US 2019/0302053 A1 Oct. 3, 2019

Related U.S. Application Data

(63) Continuation of application No. PCT/EP2017/081476, filed on Dec. 5, 2017.

(30) Foreign Application Priority Data

Dec. 5, 2016 (DE) .................. 10 2016 123 458.3

(51) Int. Cl.
*G01N 27/447* (2006.01)
*G01N 1/30* (2006.01)
(Continued)

(52) U.S. Cl.
CPC ..... *G01N 27/44743* (2013.01); *A01N 1/0294* (2013.01); *C12M 1/42* (2013.01);
(Continued)

(58) Field of Classification Search
CPC ................ C12N 13/00; C12M 1/42; G01N 27/44704; G01N 1/30
See application file for complete search history.

(56) References Cited

U.S. PATENT DOCUMENTS 5,814,200 A    9/1998  Pethig et al.
5,916,265 A *  6/1999  Hu ..................... A61L 27/3633
                                             623/23.72
(Continued)

FOREIGN PATENT DOCUMENTS

WO    2013028573 A1    2/2013
WO    2015041755 A1    3/2015
(Continued)

OTHER PUBLICATIONS

R.M. Grossfeld, A study of the Changes in Protein Composition of Mouse Brain during Ontogenetic Development, Journal of Neurochemistry, 1971 (18), p. 2265-2277. (Year: 1971).*
(Continued)

*Primary Examiner* — Luan V Van
*Assistant Examiner* — Caitlyn Mingyun Sun
(74) *Attorney, Agent, or Firm* — Thomas | Horstemeyer, LLP

(57) ABSTRACT

In a method for producing transparent biological preparations for examination by light microscopy biological tissue is electrophoretically clarified in that the tissue is immersed in an aqueous alkaline electrophoresis solution and is exposed to an electric field in the electrophoresis solution. The electrophoresis solution contains a buffer base, the cations of which have a molecular weight of at least 50 Da, at a concentration of 5 to 100 mol/m$^3$ and a non-ionic detergent at a concentration of 0.1 to 10% (w/v).

21 Claims, 3 Drawing Sheets

(51) Int. Cl.
  *C12M 1/42* (2006.01)
  *C12N 13/00* (2006.01)
  *A01N 1/02* (2006.01)
  *C07K 1/14* (2006.01)
  *C07K 1/26* (2006.01)

(52) U.S. Cl.
  CPC ............... *C12N 13/00* (2013.01); *G01N 1/30* (2013.01); *G01N 27/447* (2013.01); *C07K 1/14* (2013.01); *C07K 1/26* (2013.01); *G01N 27/44704* (2013.01)

(56) References Cited

U.S. PATENT DOCUMENTS

| | | | |
|---|---|---|---|
| 6,203,683 | B1 | 3/2001 | Austin et al. |
| 7,273,720 | B1 * | 9/2007 | Birkner .................. G01N 1/30 435/40.52 |
| 2005/0130317 | A1 | 6/2005 | Ventzki et al. |
| 2006/0231405 | A1 | 10/2006 | Hughes et al. |
| 2010/0136613 | A1 * | 6/2010 | O'Leary .............. A01N 1/0231 435/40.52 |
| 2011/0114493 | A1 | 5/2011 | Macnamara et al. |
| 2015/0144490 | A1 * | 5/2015 | Deisseroth ....... G01N 27/44743 204/461 |
| 2015/0362459 | A1 | 12/2015 | Chung et al. |

FOREIGN PATENT DOCUMENTS

| | | |
|---|---|---|
| WO | 2017096248 A1 | 6/2017 |
| WO | 2019/177492 A1 | 9/2019 |

OTHER PUBLICATIONS

Thermo Fisher Scientific—Detergents for Protein Solubilization (Year: 2021).*
PBS buffer Wiki (Year: 2021).*
Tris buffer Wiki (Year: 2021).*
M-T Ke, Super-Resolution Mapping of Neuronal Circuitry With an Index-Optimized Clearing Agent, Cell Reports, 2016 (14), p. 2718-2732. (Year: 2016).*
H, Hama, ScaleS: an optical clearing palette for biological imaging, Nature Neuroscience, 2015(18), p. 1518-1529. (Year: 2015).*
PBS_buffer (Year: 2021).*
Thermo-Fisher: Detergents for Protein Solubilization (Year: 2021).*
Closed-loop System (Year: 2021).*
CelExplorer_FocusClear (Year: 2021).*
Sung-Yon Kim et al.: "Stochastic electrotransport selectively enhances the transport of highly electromobile molecules", Proceedings National Academy of Sciences PNAS, vol. 112, No. 46, Nov. 2, 2015, pp. E6274-E6283, XP055434816, US; ISSN: 0027-8424, D01: 10.1073/pnas. 15101331112; pp. 6278-6279; figures 2-3.
English Translation of International Preliminary Report on Patentability in co-pending, related PCT Application No. PCT/EP2017/081476, dated Jun. 11, 2019.

* cited by examiner

METHOD OF PRODUCING TRANSPARENT BIOLOGICAL PREPARATIONS FOR EXAMINATION BY LIGHT MICROSCOPY

CROSS REFERENCE TO RELATED APPLICATIONS

This application is a continuation to International Application PCT/EP2017/081476 with an international filing date of Dec. 5, 2017 entitled "Method for producing transparent preparations for examination by light microscopy" and claiming priority to German Patent Application DE 10 2016 123 458.3 entitled "Verfahren zur Herstellung transparenter biologischer Präparate für eine lichtmikroskopische Untersuchung" and filed on Oct. 10, 2016, to which German Patent DE 10 2016 123 458 was granted on Mar. 15, 2018.

FIELD OF THE INVENTION

The present invention relates to a method of producing transparent biological preparations for examination by light microscopy. More particularly, the present invention relates to a method of producing transparent biological preparations for examination by light microscopy, in which biological tissue is clarified electrophoretically in that the tissue is immersed in an aqueous alkaline electrophoresis solution and subjected to an electric field in the electrophoresis solution, the electrophoresis solution containing a base and a detergent.

BACKGROUND OF THE INVENTION

Transparent biological preparations are necessary to allow for three-dimensionally imaging of the preparations by, for example, light sheet microscopy. To achieve the transparency of biological preparations, particularly haem-groups of the blood pigment hemoglobin and lipids have to be removed from the biological preparations.

A procedure for preparing biological samples for analysis by microscopy, which is also known as CLARITY method is known from US patent application publication US 2015/0 144 490 A1. In the CLARITY method, the respective sample is first fixed in a hydrogel. Only afterwards, the sample is placed in an aqueous alkaline electrophoresis solution and subjected to an electric field within this electrophoresis solution. The electrophoresis solution contains boric acid, 0.4% (w/v) sodium dodecyl sulfate (SDS) and sodium hydroxide (NaOH) for adjusting a pH-value of 8.5. The electrophoresis solution is circulated within the chamber in which the respective sample is subjected to the electric field. The temperature of the electrophoresis solution is 37-50° C., the electrical voltage applied is 10-60 V (without indication of the distance over which this voltage drops). Practically, the electrophoretic clearing according to the CLARITY method needs some days. After the electrophoretic clearing, the sample is transferred into a medium having a refractive index of 1.5, and it can additionally be stained, for example by antibody staining.

US patent application publication US 2005/0 130 317 A1 describes an apparatus for parallel analysis of biological molecules comprising a reaction room extending between two electrodes. A voltage is applied to the electrodes which causes a migration of the biological molecules introduced between the electrodes.

From international application publication WO 2017/096 248 A1 only published after the priority date of this patent application, methods for preparing and analyzing tumor tissue samples for detecting and monitoring tumors are known. The methods comprise processing a biological sample by fixing the sample in the presence of hydrogel subunits, polymerizing the hydrogel subunits to form a sample embedded in hydrogel, clearing the sample embedded in the hydrogel and marking the cleared sample embedded in hydrogel with one or more detectable markers. The clearing of the sample for example includes subjection to organic solvents, subjection to detergents, like for example Saponin, Triton X-100 and Tween-20, subjection to ionic surface active agents, like for example sodium dodecyl sulfate (SDS), and particularly electrophoresis using a buffer solution including an ionic surface active agent, particularly sodium dodecyl sulfate.

There still is a need of a method of producing transparent biological preparations for examination by light microscopy, which is less laborious and much faster than the known CLARITY method.

SUMMARY OF THE INVENTION

The present invention relates to a method of producing transparent biological preparations for examination by light microscopy. The method comprises clearing a biological tissue electrophoretically by immersing the biological tissue in an aqueous alkaline electrophoresis solution and by subjecting the biological tissue to an electric field in the electrophoresis solution. The electrophoresis solution contains a buffer base whose cations have a molecular weight of at least 50 Da in a buffer base concentration in a range from 5 to 100 mol/m$^3$ (5 to 100 mmol/l) and a non-ionic detergent in a detergent concentration in a range from 0.1 to 10% (w/v).

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
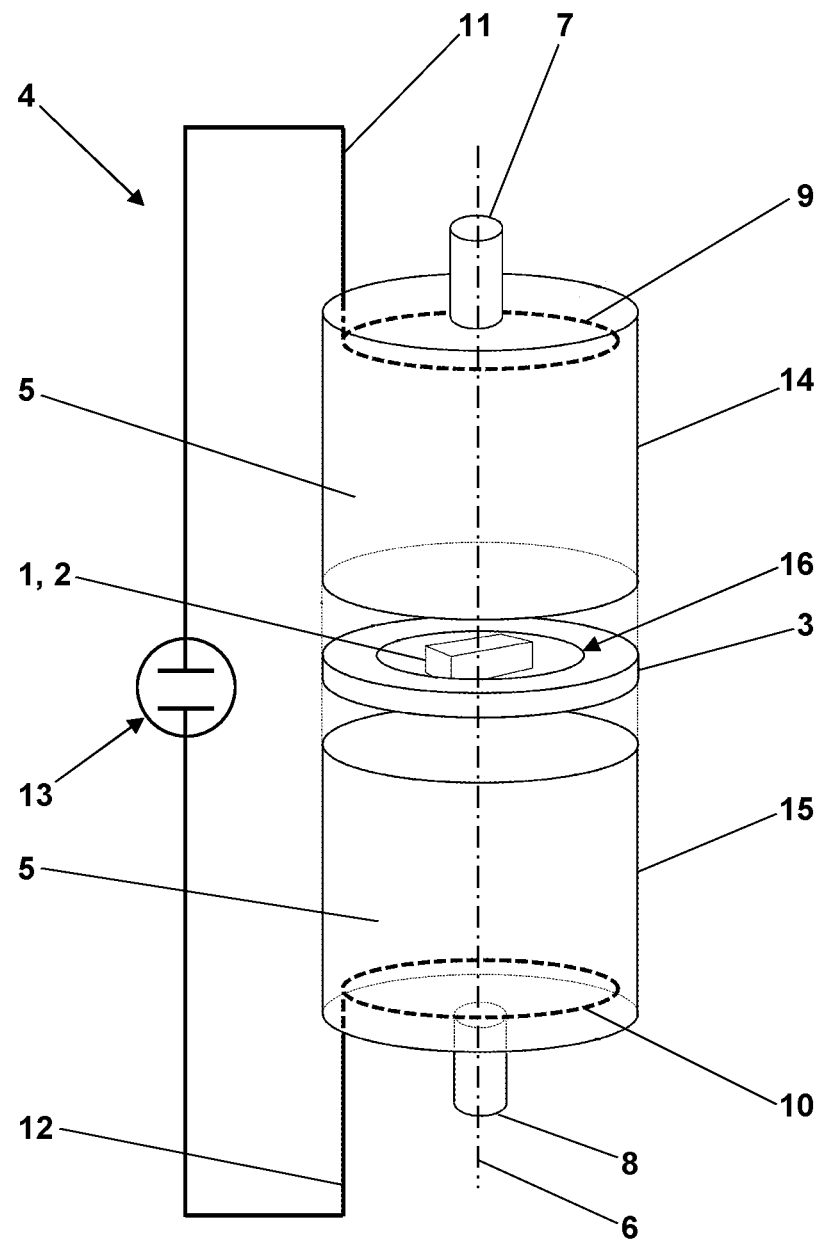
FIG. 1 is an explosion view of a reaction chamber for executing the method according to the invention.

In a method according to the present disclosure for producing transparent biological preparations for an examination by light microscopy, biological tissue is clarified electrophoreticcally in that the tissue is immersed in an aqueous alkaline electrophoresis solution and subjected to an electric field within the electrophoresis solution. The electrophoresis solution contains a buffer base whose cations have a molecular weight of at least 50 Da in a concentration of 5 to 100 mol/m$^3$ (5 to 100 mmol/l) and a non-ionic detergent in a concentration of 0.1 to 10% (w/v, i.e. weight in kilogram related to the volume in liters).

By means of the buffer base, whose cations have a molecular weight of at least 50 Da, the buffer base adjusts the desired alkaline pH-value of the electrophoresis solution, but its cations are comparatively big and immobile, particularly as compared to sodium ions. As a result, the electric field does not predominantly only cause an electric current in form of moved cations of the buffer base but, in a considerable proportion, also a current of micelles in which haem-groups and lipids are enclosed in the detergent. The electric current based on these micelles results in the desired clarification of the biological tissue in that the electric current leads the micelles and thus the haem-groups and the lipids out of the biological tissue.

By using a non-ionic detergent in the method according to the present disclosure, there is also no electrical current caused by the applied electric field in form of detergent ions which as such, like a current of the cations of the buffer base, would only be parasitic with regard to the desired clarification of the biological tissue. The results of such parasitic ion currents would inter alia be a heating up of the biological tissue without a clarification of the biological tissue associated with this heating up. Parasitic currents would also inhibit that electric fields of higher field strength could be formed over the biological tissue, as the induced high currents would heat up the biological tissue too much. Such electrical fields of higher field strength, however, are advantageous for leading even larger and correspondingly immobile micelles out of the biological tissue.

In that, in the method according to the present disclosure, both the cations of the buffer base are comparatively immobile and the detergent is non-ionic, the parasitic currents are kept small so that the efficiency of the electrophoretic clarification related to the currents flowing is enhanced considerably. Additionally, the tendency of non-ionic detergents to bind to proteins which should stay in the biological tissue is lower than the tendency of ionic detergents, like for example SDS. For this reason, the method according to the present disclosure may without problem do without fixation of the biological tissue in hydrogel, by which it is ensured in the known CLARITY method that the proteins stay in the respective biological tissue. The no longer existing necessity of the fixation of the biological tissue in hydrogel does not only have the advantage that considerably procedural efforts may be saved; it is also achieved that the mobility of the micelles which shall be led out of the biological tissue by means of the applied electrical field is not reduced by the hydrogel.

Altogether, with the method according to the present disclosure, a clarification of biological tissues for producing biological preparations for an examination by light microscopy is as a rule already achieved within a few hours with the method according to the present disclosure.

It is to be understood that the indication "non-ionic detergent" is not to be understood in that this indication solely means a detergent having an ionicity of zero. Instead, the indication relates to all detergents which have no pronounced ionicity, i.e. at least essentially no ionicity. The non-ionic detergent may further be selected such as to have as little affinity to proteins as possible. Based on these guidelines, the person skilled in the art is without problem able to select suitable non-ionic detergents.

Practical testing of the method according to the present disclosure have shown that at least the following detergents are suitable as non-ionic detergents: Tween 20, Tween 80, Triton X45, Triton X100, Triton X102, n-octyl-beta-D-glucopyranoside, octylphenolethoxylate, Brij35 and Nonidet P40. Particularly good properties for use in the method according to the present disclosure are displayed by the non-ionic detergents Tween 80, Triton X45, Triton X102, n-octyl-beta-D-glucopyranosidd, Brij35 and Nonidet P40. The most favorable properties are displayed by Tween 80, Triton X102 and Nonidet P40.

The non-ionic detergent which is used in the method according to the present disclosure may also be composed of more than one of the above mentioned detergents. The mixture of the detergents may purposefully be adjusted to the different components of the respective biological tissue which are to be removed in the electrophoretic clearing.

The concentration of the buffer base in the electrophoresis solution may be in a range from 10 to 50 mol/m$^3$ or in a range from 15 to 25 mol/m$^3$, i.e. about 20 mol/m$^3$.

The concentration of the non-ionic detergents in the electrophoresis solution may be 0.5 to 1.5% (w/v), i.e. about 1% (w/v).

The molecular weight of the cations of the buffer base may be at least 100 Da. Buffer bases which fulfill this requirement to an increasing extent in the sequence of their nomination are Tris, Bicine and BisTris.

A maximum temperature of the electrophoresis solution during the electrophoretic clearing may be kept in a range from 20 to 90° C. In any case, the temperature is to be kept below the boiling point of the electrophoresis solution. The maximum temperature of the electrophoresis solution during the electrophoretic clearing may be kept in a range from 40 to 60° C., i.e. at about 50° C. With a higher temperature, however, it may be achieved that binding points for antibodies on proteins can be unmasked thermally so that these proteins may afterwards be marked with the antibodies.

In the method according to the present disclosure, an increase in temperature of the biological tissue results from the input of electric energy which is transformed into heat. This is generally unavoidable. In the method according to the present disclosure, however, the achieved clarification of the biological tissue related to the input of electric energy is particularly high.

Thus, it is particularly easy to limit the temperature of the biological tissue to a maximum temperature in the ranges mentioned without, for example, needing an active cooling of the electrophoresis solution.

In the execution of the method according to the present disclosure, a pH-value of the electrophoresis solution can be kept in a range from 8 to 9 during the electrophoretic clearing. The electric current flowing as a result of the applied electric field typically reduces the pH-value of the electrophoresis solution, even if the buffer base provides for a reservoir of OH-groups. To keep the efficiency of the clarification of the biological tissue high, it is thus useful to keep the pH-value of the electrophoresis solution in the alkaline range mentioned. For this purpose, fresh buffer base may be added during the electrophoretic clearing. The detergent used up by leading the micelles out under the influence of the electric fields may also be re-filled during the electrophoretic clearing by adding fresh detergent to the electrophoresis solution. A maximum efficiency of the method according to the present disclosure is achieved, when the electrophoresis solution is continuously exchanged by unused electrophoresis solution.

In the method according to the present disclosure, an electric power which is supplied to the electrophoresis solution and the tissue immersed therein can be closed-loop controlled during the electrophoretic clearing. This control may be made depending on the temperature of the biological tissue or the electrophoresis solution, respectively, or to a constant value which ensures keeping a certain maximum temperature. At least, the electric power may be controlled to such a fixed value for a part of the duration of the electrophoretic clearing. If the clarification of the biological tissue has already progressed to a far extent or the electrophoresis solution has already essentially been used up, the further control of the electric power to a fixed value is often no longer suitable.

The progress of the clearing of the biological tissue may be monitored by registering an electric resistance of the electrophoresis solution and the biological tissue immersed therein. Initially, the electric resistance decreases, i.e. the electric conductivity increases, when the micelles which are to be led out are formed in the biological tissue. With the consumption of the electrophoresis solution or when essential parts of the haem-groups and lipids to be removed have already been led off, the resistance increases again and the electric conductivity decreases again, respectively. Thus, the conditions of the electrophoretic clarification in the method according to the present disclosure may then be changed and/or the electrophoretic clearing may be terminated, when the electric resistance goes beyond or its time rate of change goes below a predetermined threshold value.

Prior to being cleared electrophoretically according to the method according to the present disclosure, the biological tissue may already be subjected to other treatments. Fixing the biological tissue, for example with formaldehyde which, in contrast to a hydrogel used for fixation, does not delimit the mobility of the micelles, belongs to these treatments. Further, washing the biological tissue, for example with water or also with the electrophoresis solution which is later used during the electrophoretic clearing, belongs to the optional steps prior to the actual electrophoretic clearing. Further, the biological tissue, before being cleared electrophoretically, may be incubated in an aqueous alkaline solution. In this incubating it proves to be advantageous, if the following parameters are at least kept partially: The incubation takes place for a period of 30 to 120 min or from 45 to 90 min. The incubating takes place at a temperature from 20 to 50° C. or from 35 to 40° C., i.e. of about 37.5° C. The aqueous alkaline solution comprises an alkali concentration of 50 to 2,000 mol/m$^3$ or from 100 to 1,000 mol/m$^3$. The aqueous alkaline solution comprises NaOH for providing its alkali concentration. The aqueous alkaline solution comprises a $C_{1-6}$-alcohol at a concentration from 10 to 70% (v/v) or from 40 to 60% (v/v). The aqueous alkaline solution comprises ethanol; and the aqueous alkaline solution comprises a detergent in a concentration from 0.1 to 10% (w/v) or from 0.5 to 2% (w/v).

In addition to the electrophoretic clearing in the alkaline aqueous electrophoresis solution, the biological tissue may be incubated in an aqueous acidic solution and then be subjected to an electric field within the aqueous acidic electrophoresis solution for further electrophoretic clarification.

In incubating the tissue in the aqueous acidic solution, at least one of the following parameters may be kept: The incubating takes place for 30 to 120 min or for 45 to 90 min. The incubating takes place at 20 to 50° C. or at 35 to 40° C. The aqueous acidic solution comprises a proton concentration from 50 to 2,000 mol/m$^3$ or from 100 to 1,000 mol/m$^3$. The aqueous acidic solution comprises trichloroacetic acid to provide its proton concentration. The aqueous acidic solution comprises a $C_{1-6}$-alcohol in a concentration from 10 to 70% (v/v) or from 40 to 60% (v/v). The aqueous acidic solution comprises ethanol, and the aqueous acidic solution comprises a detergent in a concentration from 0.1 to 10% (w/v) or from 0.5 to 2% (w/v). Further, the aqueous acidic electrophoresis solution may keep at least one of the following parameters: The aqueous acidic electrophoresis solution contains a buffer acid in a concentration from 5 to 100 mol/m$^3$ and a non-ionic detergent in a concentration from 0.1 to 10% (w/v); and the aqueous acidic electrophoresis solution includes acetic acid in a concentration from 10 to 50 mol/m$^3$ and a non-ionic detergent in a concentration from 0.5 to 2% (w/v).

After the biological tissue has been cleared electrophoretically, the tissue may be prepared further for the examination by light microscopy. At least one of the following steps may be made: The biological tissue is incubated with at least one antibody. The biological tissue is subjected to an electric field in a solution of the antibody. The biological tissue is stained with at least one dye. The biological tissue is subjected to an electric field in a solution of the dye. The biological tissue is washed with at least one organic solvent. The biological tissue is washed with xylol or dichloromethane. The biological tissue is immersed in a solution with a refractive index in a range from n=1.4 to n=1.6. The refractive index range from n=1.4 to n=1.6, i.e. of about n=1.5, means that the solution has the same refractive index as the cleared biological tissue. Thus, there is no scattering at the boundary surfaces of the biological tissue in the examination by light microscopy.

Particularly, the biological tissue, after it has been cleared electrophoretically, may be placed in an aqueous solution or in a sugar or polyol solution having a refractive index in the range mentioned of about n=1.5. Alternatively, the biological tissue, after it has been cleared electrophoretically, may be dehydrated in a series of alcohols with increasing alcohol concentration, or the cleared tissue may be placed in an organic solvent, in methyl salicylate or in a methyl salicylate solution having a refractive index in a range of about n=1.5.

For actually executing the method according to the present disclosure, the tissue may be arranged in a reaction chamber for the electrophoretic clearing, the reaction chamber comprising a reaction room which is rotation symmetric about a vertical axis, has a waist and is to be filled with the electrophoresis solution, a downwardly open ring channel in the reaction room below the waist, which is connected to a gas removal channel leading upwards, a first ring-shaped electrode within the ring channel or in the reaction room below the ring channel, and a second ring-shaped electrode in the reaction room above the waist. The first and the second electrodes are then connected to the two outputs of a directed current source to subject the biological tissue to the electric field. The tissue is arranged in a reduced free cross section of the reaction room in the waist, where an about homogeneous electric field between the electrodes is concentrated. Via the gas removing channel, gas bubbles formed at the lower electrode and ascending therefrom may be led off so that the bubbles do not accumulate in the reaction room and hinder the flow of electric current. Further deformation of oxyhydrogen gas is avoided, if the gas bubbles include hydrogen formed by hydrolysis which could mix up with oxygen formed by hydrolysis at the upper electrode. The reaction chamber may have further features as they are known from US 2005/0130317 A1.

In an embodiment of the method according to the present disclosure for preparing transparent biological preparations for an examination by light microscopy, a sample 1 of biological tissue 2, with the aid of a sample holder 3, is arranged in a reaction chamber 4 which is depicted in FIG. 1 in an explosion view. The reaction chamber 4 has a reaction room 5 which is rotationally symmetric about a vertical axis 6. In the reaction room 5, the biological tissue 2 is arranged at about half of its height, wherein, by means of the sample holder 3, a waist, i.e. a reduction in diameter of the reaction room 5, is formed. The biological tissue is arranged in the area of the reduced free cross-section 16 of the reaction room 5 in the waist. In executing the method according to the present disclosure, the reaction room 5 is filled at least with an aqueous alkaline electrophoresis solution. All other solutions with which the biological tissue 2 gets into contact in the execution of the method according to the present disclosure may also be filled in the reaction room 5 or led through the reaction room 5. For this purpose, the reaction room 5 has an upper connector 7 and a lower connector 8. These connectors 7 and 8 may not only be used during the treatment of the biological sample 2 for altering the composition of the solution in the reaction room 5 or for even exchanging it by another solution but also for circulating the respective solution through the reaction room 5. In this circulation, the respective solution may, for example, be led through a heat exchanger to temper it, or the solution may be regenerated with regard to consumed components.

For an electrophoretic clarification of the biological tissue 2 to remove particularly haem-groups and lipids therefrom, an upper electrode 9 and a lower electrode 10 are provided which immerge into the solution present in the reaction room. By applying a voltage between the electrodes 6 and 9, an electric field is formed over the biological tissue 2 which provides the driving electric force for the electrophoretic clarification. For applying the voltage between the electrodes 9 and 10, connection lines 11 to the upper electrode 9 and 12 to the lower electrode are provided by which the electrodes 9 and 10 are connected to a direct voltage source 13. The electrodes 9 and 10 are ring-shaped to cause an as homogenous electric field as possible in the area of the waist, i.e. of the free cross-section of the sample holder 3 in which the biological tissue 2 is arranged. It is to be understood that both the sample holder 3 and the two adjacent parts 14 and 15 of the sample chamber are made of electrically isolating material.

Figure 2:
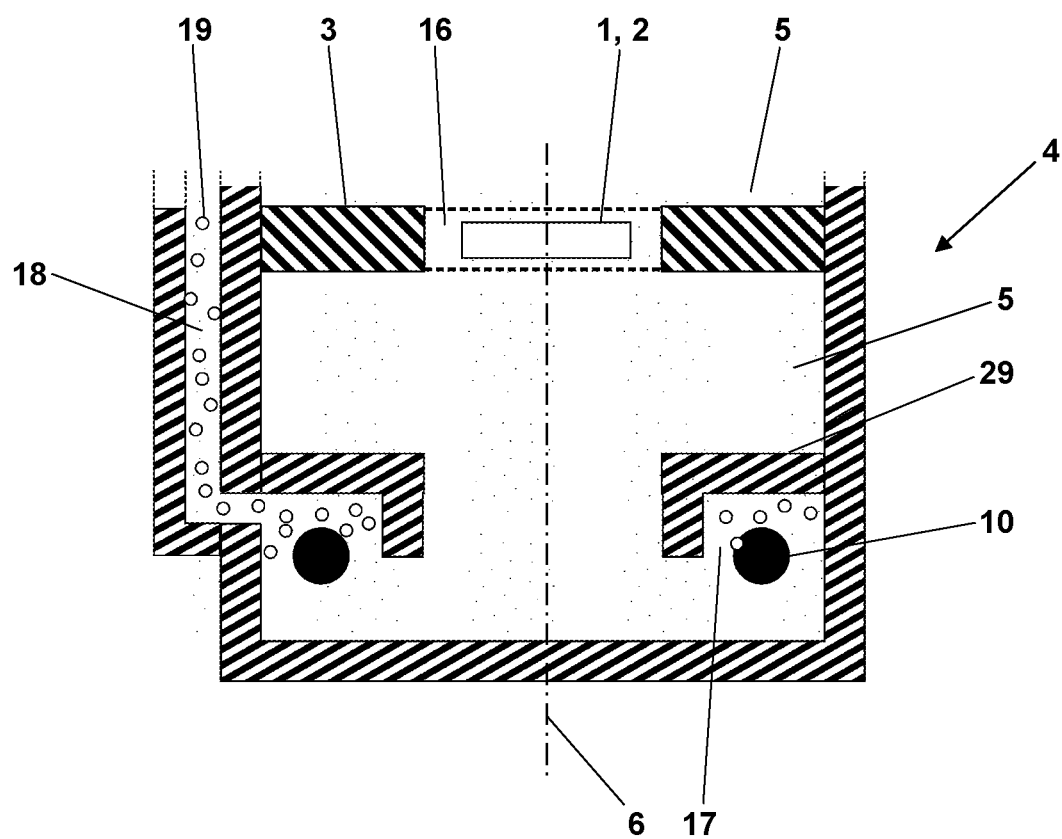
FIG. 2 shows a detail of a modified embodiment of the reaction chamber in a vertical section.

The detail of another embodiment of the reaction chamber 4, which is depicted in FIG. 2 in a vertical section, shows the lower part of the reaction room 5 in which the sample holder 3 is inserted with the sample 1 so that the biological tissue 2 is arranged in the free cross-section 16 of the waist of the reaction room 5 by means of the sample holder 3. A lower connector 8 to the reaction room 5 is not depicted here, but may be present as in FIG. 1. The lower electrode 10 is arranged partially below and partially within a ring channel 17 which is closed in upper direction and which is formed by an insert 29 in the sample chamber. The downwardly open ring channel 17 is connected to an upwardly leading gas removal channel 18 to remove gas bubbles 19 ascending from the electrode 10 as a result of the voltage present, and, for example, including hydrogen formed by hydrolysis, in a controlled way so that the bubbles do not accumulate in the reaction room 5 and thus hinder the current flow through the reaction room 5 and so that also the formation of oxyhydrogen gas in the reaction room 5 is avoided.

Figure 3:
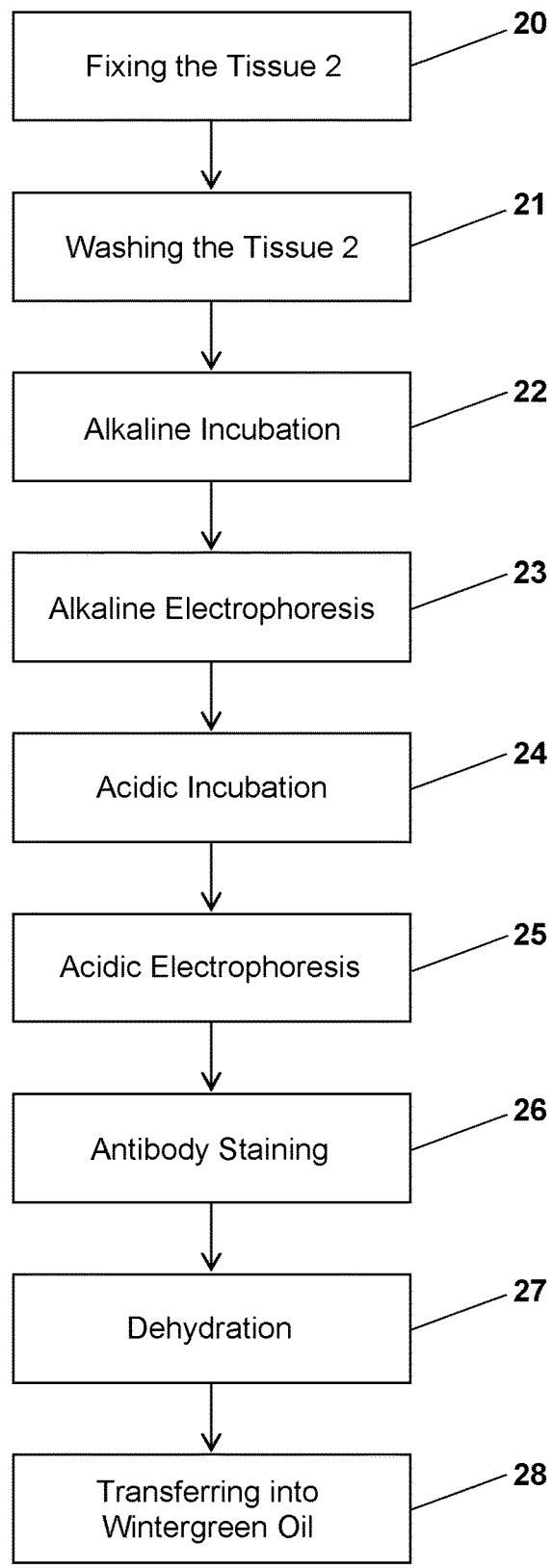
FIG. 3 is a flowchart of an embodiment of the method according to the invention.

The method according to the present disclosure illustrated in FIG. 3 in a block diagram starts with fixing 20 the biological tissue 2 for example with formaldehyde. Washing 21 the tissue 2, for example with water, follows thereto. In the course of the execution of the method according to the present disclosure, further washing steps may be inserted, which are not pointed out in FIG. 3. It generally applies that the tissue 2, prior to any longer lasting treatment in a solution, as it will be explained in the following, may initially be washed with this solution.

An alkaline incubation 22 takes place, for example, for one hour at 37° C. in an aqueous solution with 100 mol/m$^3$ NaOH, 50% EtOH and 1% (w/v) of a detergent. A subsequent alkaline electrophoresis 23 takes place, for example, for 45 min at 50° C. in an aqueous alkaline electrophoresis solution with 20 mol/m$^3$ Tris and 1% (w/v) of the respective detergent. The actual electrophoresis takes place at a direct voltage between the electrodes 9 and 10 of 1,000 V at maximum, a maximum current of 150 mA and a power limit of 10 W. This may result, for example, in an average voltage of 500 V at an average current of 20 mA. With interposition of a washing step not depicted, an acidic incubation 24 may follow. The acidic incubation 24 may correspond to the alkaline incubation 22 except that it takes place under addition of trichloroacetic acid instead of NaOH. Similarly, in a subsequent acidic electrophoresis 25 generally the same conditions may prevail as in the alkaline electrophoresis 23 except that trichloroacetic acid is used instead of Tris. Afterwards or at any suitable point of the method according to the present disclosure, an antibody staining 26 takes place, i.e. an immunologic staining of certain proteins which are still present in the tissue 2 after the electrophoretic clearing. Here, antibodies are used which specifically bind to these proteins and which either carry a dye themselves or which are subsequently marked with a dye. If the cleared and, if given, stained biological tissue 2 is not to be examined by light microscopy in an aqueous solution, a dehydration 27 takes place to which a transfer 28 into a medium with a refractive index of the cleared tissue of about 1.5 follows. A medium suitable for this purpose is wintergreen oil. Afterwards, the tissue is, for example, suitable for an examination by light microscopy under application of a light sheet technique. As compared to the known CLARITY method, the method according to the present disclosure displays a very short total method duration of a few hours. Here, it is also to be considered that the acidic incubating 24 and the acidic electrophoresis 25 are often not necessary to sufficiently clear the biological tissue 2.

According to the following protocol for executing the method according to the present disclosure samples 1 of pig lung tissue of about 250 mg each have successfully been cleared. Fixing 20 of the tissue 2 takes place in formaldehyde. Washing 21 of the tissue 2 takes place for 10 min with water. The alkaline incubation 22 took place for one hour at 37° C. in aqueous solution with 500 mol/m$^3$ NaOH, 50% (v/v) EtOH and 1% (w/v) of a non-ionic detergent. The alkaline electrophoresis 23 took place for 45 min in aqueous electrophoresis solution with 20 mol/m$^3$ Tris and 1% (w/v) of the respective non-ionic detergent. Between the electrodes 9 and 10, a direct voltage of 1,000 V at maximum was present, and the maximum current was 150 mA, wherein the power was delimited to 10 W. The dehydration 27 took place in four 30 min steps with 50%, 70%, 90% and 100% ethanol. Transferring 28 took place into wintergreen oil. Using this protocol, the different tested non-ionic detergents resulted in differently good results which were rated as follows according to an assessed scale from 0 (bad clearing, darkly stained sample) to ++++ (good transparency and no staining):

0: no detergent
+: Tween 20, Triton X100
++: n-octyl-beta-D-glucopyranoside, Brie 35
+++: Nonidet P40, Triton X45 (milky solution), Tween 80
++++: Triton X102

In a further experiment, the correlation between the course of the electric resistance in the alkaline electrophoresis, the blood load of the tissue 2 and the clearing result was examined. The electric resistance decreases at the beginning of the alkaline electrophoresis. This can be attributed to the formation and release of the micelles containing the haem-groups and lipids as mobile charge carriers which may afterwards be led out of the tissue 2 by means of the electric field. With high blood load of the tissue, more such charge carriers may form. Correspondingly, the electric resistance decreases much quicker and reaches a smaller minimum value. With the consumption of the components of the electrophoresis solution forming the charge carriers, the resistance increases again, and also when the components of the tissue forming the charge carriers, i.e. the haem-groups and lipids, are already essentially removed out of the tissue. This course of the electric resistance can purposefully be used for controlling the alkaline electrophoresis, particularly to notice the point in time at which the alkaline electrophoresis may suitably be terminated. Further, this course of the electric resistance is a proof of the correctness of the considerations forming the basis of the method according to the present disclosure to keep the electric conductivity of the electrophoresis solution as such as small as possible and to care for that, so far as possible, only charge carriers are formed which actually include substances to be removed out of the tissue for clearing it, like haem-groups and lipids. The electric current flowing under these conditions efficiently results in the electrophoretic clarification of the tissue 2. In this way, both electric heating of the sample 2 by parasitic electric currents and parasitic electric currents in practice inhibiting the formation of high field strengths of the electric field formed over the sample, that are needed to exert sufficiently high electric forces on the comparatively big micelles including haem-groups and lipids to lead them out of the biological tissue 2, are avoided.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of producing transparent biological preparations for examination by light microscopy, the method comprising:
    incubating a biological tissue in an aqueous alkaline solution, the aqueous alkaline solution comprising an alkali metal hydroxide concentration of at least 50 mol/m$^3$,
    clearing the biological tissue electrophoretically by:
        immersing the biological tissue in an aqueous alkaline electrophoresis solution, and
        subjecting the biological tissue to an electric field in the electrophoresis solution,
    wherein the electrophoresis solution contains:
        a buffer base whose cations have a molecular weight of at least 50 Da in a buffer base concentration in a range from 5 to 100 mol/m$^3$, and
        a non-ionic detergent in a detergent concentration in a range from 0.1 to 10% (w/v).

2. The method of claim 1, wherein the non-ionic detergent at least predominantly consists of at least one substance which is selected from a group of substances consisting of: Tween 20, Tween 80, Triton X45, Triton X100, Triton X102, n-octyl-beta-D-glucopyranoside, octylphenolethoxylate, Brij35 and Nonidet P40.

3. The method of claim 1, wherein
    the buffer base concentration is in a range from 10 to 50 mol/m$^3$,
    the detergent concentration is in a range from 0.5 to 1.5% (w/v), and
    the molecular weight of the cations of the buffer base is at least 100 Da.

4. The method of claim 1, wherein the buffer base at least predominantly consists of at least one substance which is selected from a group of substances consisting of: Tris, Bicine and BisTris.

5. The method of claim 1, wherein, in the step of electrophoretic clearing, a maximum temperature of the electrophoresis solution is kept in a range from 20 to 90° C. below a boiling point of the electrophoresis solution.

6. The method of claim 1, wherein, in the step of electrophoretic clearing, a maximum temperature of the electrophoresis solution is kept in a range from 40 to 60° C.

7. The method of claim 1, wherein, in the step of electrophoretic clearing, a pH-value of the electrophoresis solution is kept in a range from 8 to 9.

8. The method of claim 1, wherein, in the step of electrophoretic clearing, at least one of fresh buffer base and fresh detergent is added to the electrophoresis solution.

9. The method of claim 8, wherein, in the step of electrophoretic clearing, the electrophoresis solution is continuously changed.

10. The method of claim 1, wherein, in the step of electrophoretic clearing, an electric power delivered to the electrophoresis solution and the tissue immersed therein is closed-loop controlled.

11. The method of claim 10, wherein the electric power is closed-loop controlled to a constant value at least for a part of a duration of the step of electrophoretic clearing.

12. The method of claim 1, wherein, in the step of electrophoretic clearing, an electric resistance of the electrophoresis solution and the biological tissue immersed therein is registered, and conditions of the step of electrophoretic clearing are changed or the step of electrophoretic clearing is terminated, when the electric resistance goes beyond a predetermined threshold value or a time rate of change thereof below a predetermined threshold value.

13. The method of claim 1, further comprising, prior to the step of electrophoretic clearing, at least one of the following steps:
    fixing the biological tissue,
    fixing the biological tissue with formaldehyde,
    washing the biological tissue,
    washing the biological tissue with water,
    washing the biological tissue with the electrophoresis solution.

14. The method of claim 1, wherein, in incubating the biological tissue in the aqueous alkaline solution, at least one of the following parameters is kept:
    the incubating takes place for 30 to 120 min or for 45 to 90 min;
    the incubating takes place at 20 to 50° C. or at 35 to 40° C.;
    the alkali metal hydroxide concentration is in a range from 100 to 1,000 mol/m$^3$;
    the aqueous alkaline solution comprises NaOH;
    the aqueous alkaline solution comprises a $C_{1-6}$-alcohol in a concentration from 10 to 70% or 40 to 60% (v/v);
    the aqueous alkaline solution comprises ethanol; and
    the aqueous alkaline solution comprises a detergent in a concentration from 0.1 to 10% or from 0.5 to 2% (w/v).

15. The method of claim 1, further comprising, prior to or after the step of electrophoretic clearing,
   incubating the biological tissue in an aqueous acidic solution and then,
   subjecting the biological tissue to an electric field in an aqueous acidic electrophoresis solution.

16. The method of claim 15,
   wherein, in the step of incubating the tissue in the aqueous acidic solution, at least one of the following parameters is kept:
      the incubating takes place for 30 to 120 min or for 45 to 90 min;
      the incubating takes place at 20 to 50° C. or at 35 to 40° C.;
      the aqueous acidic solution comprises a proton concentration from 50 to 2,000 mol/m$^3$ or from 100 to 1,000 mol/m$^3$;
      the aqueous acidic solution comprises trichloroacetic acid;
      the aqueous acidic solution comprises a $C_{1-6}$-alcohol in a concentration from 10 to 70% or 40 to 60% (v/v);
      the aqueous acidic solution comprises ethanol; and
      the aqueous acidic solution comprises a detergent in a concentration from 0.1 to 10% or from 0.5 to 2% (w/v); and
   wherein, in the step of subjecting the biological tissue to an electric field in the aqueous acidic electrophoresis solution, at least one of the following parameters is kept:
      the aqueous acidic electrophoresis solution contains a buffer base in a concentration from 5 to 100 mol/m$^3$ and the non-ionic detergent in a concentration from 0.1 to 10% (w/v); and
      the aqueous acidic electrophoresis solution contains trichloroacetic acid in a concentration from 10 to 50 mol/m$^3$ and the non-ionic detergent in a concentration from 0.5 to 2% (w/v).

17. The method of claim 1, further comprising, after the step of electrophoretic clearing, at least one of the following steps:
   incubating the biological tissue with an antibody,
   subjecting the biological tissue in a solution of an antibody to an electric field,
   staining the biological tissue with a dye,
   subjecting the biological tissue to an electric field in a solution of a dye,
   washing the biological tissue with an organic solvent,
   washing the biological tissue with xylol or dichloromethane, and
   transferring the biological tissue in a solution having a diffractive index in a range from n=1.4 to n=1.6.

18. The method of claim 1, further comprising, after the step of electrophoretic clearing, at least one of the following steps:
   transferring the biological tissue in an aqueous solution having a refractive index in a range from n=1.4 to n=1.6; and
   transferring the biological tissue in a sugar or polyol solution with a refractive index in a range from n=1.4 to n=1.6.

19. The method of claim 1, further comprising, after the step of electrophoretic clearing, at least one of the following steps:
   dehydrating the biological tissue in an alcohol series with ascending alcohol concentration,
   transferring the biological tissue in an organic solvent having a refractive index in a range from n=1.4 to n=1.6; and
   transferring the biological tissue in methylsalicylate or a methylsalicylate solution having a refractive index in a range from n=1.4 to n=1.6.

20. The method of claim 1, wherein the biological tissue is not fixed in a hydrogel.

21. A method of producing transparent biological preparations for examination by light microscopy, the method comprising:
   clearing a biological tissue electrophoretically by:
      immersing the biological tissue in an aqueous alkaline electrophoresis solution, and
      subjecting the biological tissue to an electric field in the electrophoresis solution,
   wherein the electrophoresis solution contains:
      a buffer base whose cations have a molecular weight of at least 50 Da in a buffer base concentration in a range from 5 to 100 mol/m$^3$, and
      a non-ionic detergent in a detergent concentration in a range from 0.1 to 10% (w/v),
   wherein, in the step of electrophoretic clearing, the biological tissue is arranged in a reaction chamber for the electrophoretic clearing, the reaction chamber comprising
      a reaction room to be filled with the electrophoresis solution, the reaction room being rotationally symmetric about a vertical axis and having a waist,
      a downwardly open ring channel in the reaction room below the waist, the ring channel being connected to an upwardly leading gas removal channel,
      a first ring-shaped electrode within the ring channel or in the reaction room below the ring channel, and
      a second ring-shaped electrode in the reaction room above the waist,
      wherein the first and the second ring-shaped electrodes are connected to two outputs of a direct current source; and
   wherein the biological tissue is arranged in a reduced free cross-section of the reaction room in the waist.

\* \* \* \* \*